United States Patent

Amano et al.

[11] Patent Number: 6,045,562
[45] Date of Patent: Apr. 4, 2000

[54] CORNEA SURGICAL OPERATION APPARATUS

[75] Inventors: Masanori Amano; Masahiro Sugimura, both of Aichi; Takashi Hagiwara, Kawaguchi, all of Japan

[73] Assignee: Nidek Co., Ltd., Japan

[21] Appl. No.: 09/108,966

[22] Filed: Jul. 2, 1998

[30] Foreign Application Priority Data

Jul. 3, 1997 [JP] Japan .................................... 9-194833

[51] Int. Cl.[7] .................................................. A61F 9/00
[52] U.S. Cl. .................................................. 606/166
[58] Field of Search ........................ 606/166, 4, 161

[56] References Cited

U.S. PATENT DOCUMENTS

| Re. 35,421 | 1/1997 | Ruiz et al. | 606/166 |
|---|---|---|---|
| 4,662,370 | 5/1987 | Hoffmann et al. | 606/166 |
| 4,903,695 | 2/1990 | Warner et al. | 606/4 |
| 5,586,980 | 12/1996 | Kremer et al. | 606/166 |
| 5,591,185 | 1/1997 | Kilmer et al. | 606/166 |
| 5,595,570 | 1/1997 | Smith | 606/166 |
| 5,624,456 | 4/1997 | Hellenkamp | 606/166 |

*Primary Examiner*—Michael Buiz
*Assistant Examiner*—(Jackie) Tan-Uyen Ho
*Attorney, Agent, or Firm*—Finnegan, Henderson, Farabow, Garrett & Dunner, L.L.P.

[57] ABSTRACT

A cornea surgical operation apparatus for incising a cornea of a patient's eye into a layer comprises a fixing device having an opening put into contact with the surface of the cornea and for being fixed to a peripheral part of the cornea with the opening as a center, a press device for nearly flat pressing the cornea protruded from the opening, a blade for cutting out the cornea pressed into a nearly flat shape by the press device, a movement device for moving the blade in such a way that it passes a center of the opening, and a rotation device for rotating the blade moved at least to a Bowman membrane by the movement device with the center of the opening as the center of rotation.

9 Claims, 7 Drawing Sheets

BLADE

CORNEA SURGICAL OPERATION APPARATUS

BACKGROUND OF THE INVENTION

1. Field of the Invention

The present invention relates to a cornea surgical operation apparatus for incising the cornea of a patient's eye into a layer when a cornea surgical operation for correcting refraction is performed.

2. Description of Related Art

In recent years, a cornea surgical operation for correcting refraction referred to as a Laser in Situ Keratomileusis (LASIK) operation has received widespread attention. In this operation, after a flap is formed by incising a cornea of 150 μm thick from the epithelium of the cornea to the stroma of the cornea into a layer with one end of the cornea left as a hinge, the stroma of the cornea is ablated by the amount of corrective refraction with excimer laser and then the flap is restored. In this surgical operation, a cornea surgical operation apparatus referred to as a Microkeratome is used.

As the Microkeratome, an apparatus has been known that the cornea protruded from the opening of a suction part attracted by suction and attached to the peripheral part of the cornea (from the limbus of the cornea to a conjunctiva) is pressed flat by a cornea pressing member and then that the cornea is incised into a layer in a nearly uniform thickness by straight moving a blade (cutting edge) in the direction of a hinge while it is being vibrated transversely. It is because there is a limit to the formation of the sharp angle of the cutting edge of the blade itself, and because the considerable hard Bowman membrane (under the epithelium of the cornea) is hard to incise only by the straight movement of the blade.

Figure 7:
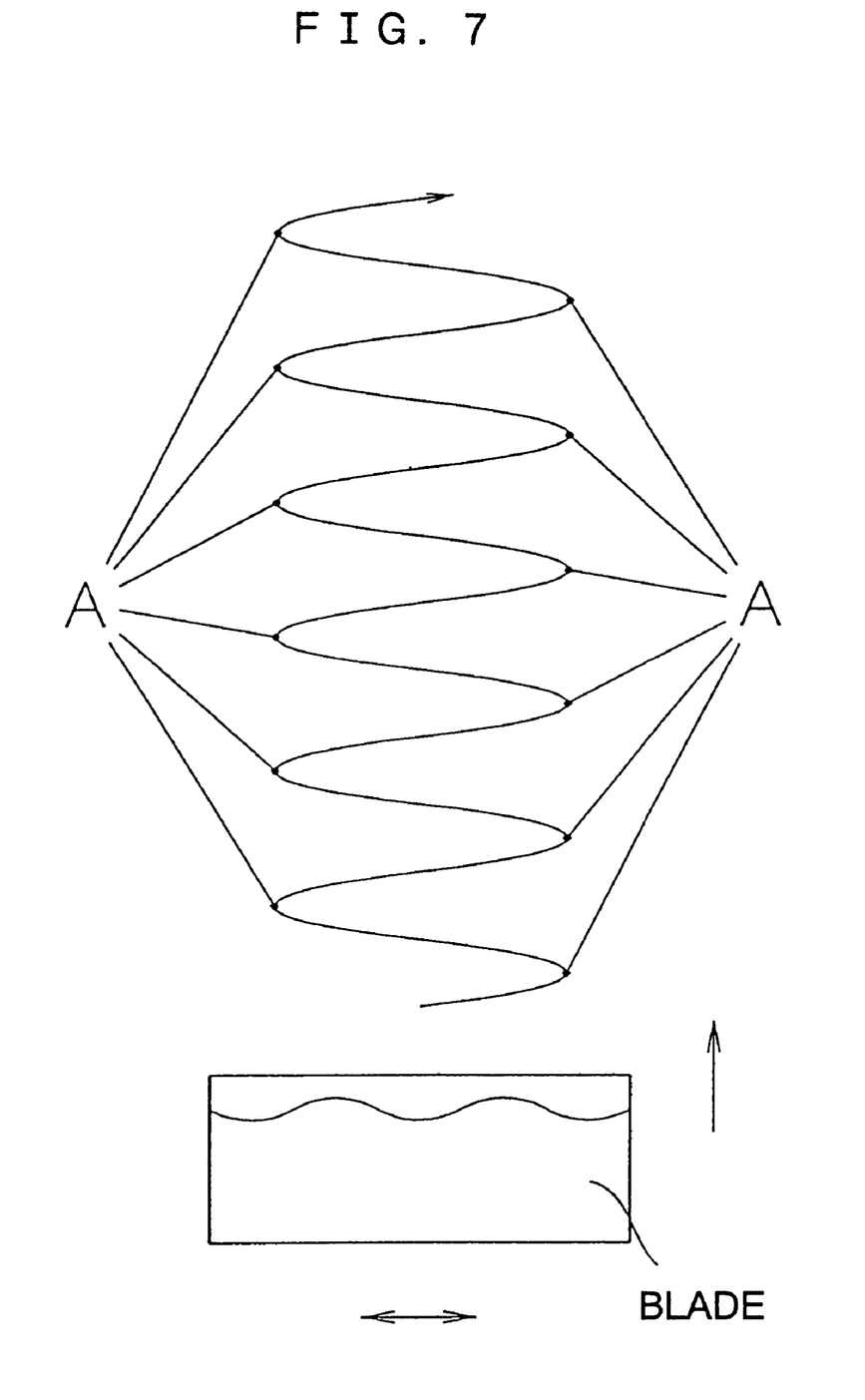
FIG. 7 is an illustration of the moving path of a blade a conventional cornea surgical operation apparatus.

However, when the blade is vibrated transversely for incising, since a speed in transverse direction becomes zero at the limit point of movement in the transverse vibration and a speed in the straight movement is constant, the force for cutting the cornea is reduced to the minimum at the point A as shown in FIG. 7, which results in producing a defect that the cut cross section of the cornea is made nonuniform.

SUMMARY OF THE INVENTION

The present invention has been made in consideration of the above-described problems and the object of the present invention is to provide a cornea surgical operation apparatus by which the Bowman membrane can be easily incised and a uniform layered cut cross section can be obtained.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, there is provided a cornea surgical operation apparatus for incising a cornea of a patient's eye into a layer, the apparatus comprising fixing means having an opening put into contact with the surface of the cornea and for being fixed to a peripheral part of the cornea with the opening as a center, press means for nearly flat pressing the cornea protruded from the opening, a blade for cutting out the cornea pressed into a nearly flat shape by the press means, movement means for moving the blade in such a way that it passes a center of the opening, and rotation means for rotating the blade moved at least to a Bowman membrane by the movement means with the center of the opening as the center of rotation.

DESCRIPTION OF THE PREFERRED EMBODIMENTS

Figure 1:
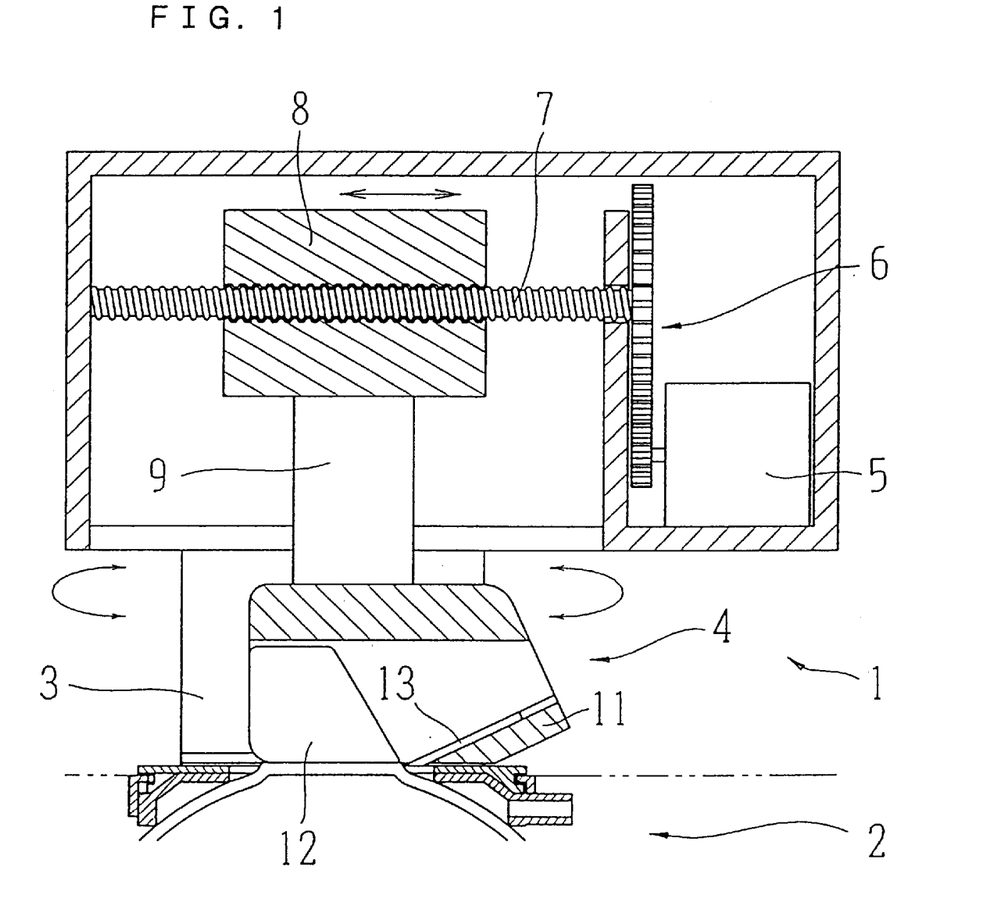
FIG. 1 is a cross sectional view of the main part of a cornea surgical operation apparatus of a preferred embodiment according to the present invention.

Embodiments according to the present invention will be described below with reference to the drawings. FIG. 1 is a cross sectional view of the main part of a cornea surgical operation apparatus of a preferred embodiment according to the present invention.

A reference numeral 1 denotes a base part and 2 denotes a suction part. The base part 1 can be separated from the suction part 2 and is rotatably connected to the suction part 2. The base part 1 is generally divided into a base box part 3 and a cutting head part 4 for incising a cornea in a layer. A drive motor 5, a gear 6, a feed screw 7 which is a rotation shaft, a moving block 8 which moves along the feed screw 7, a connecting shaft 9 for connecting and supporting the cutting head part 4 and the moving block 8, and the like are provided on the top of the base box part 3.

The rotation by the drive motor 5 is reduced by the gear 6 and is transmitted to the feed screw 7 to rotate it. If the feed screw 7 is rotated, the moving block 8 is straight moved to straight move the cutting head part 4 via the connecting shaft 9.

Figure 2:
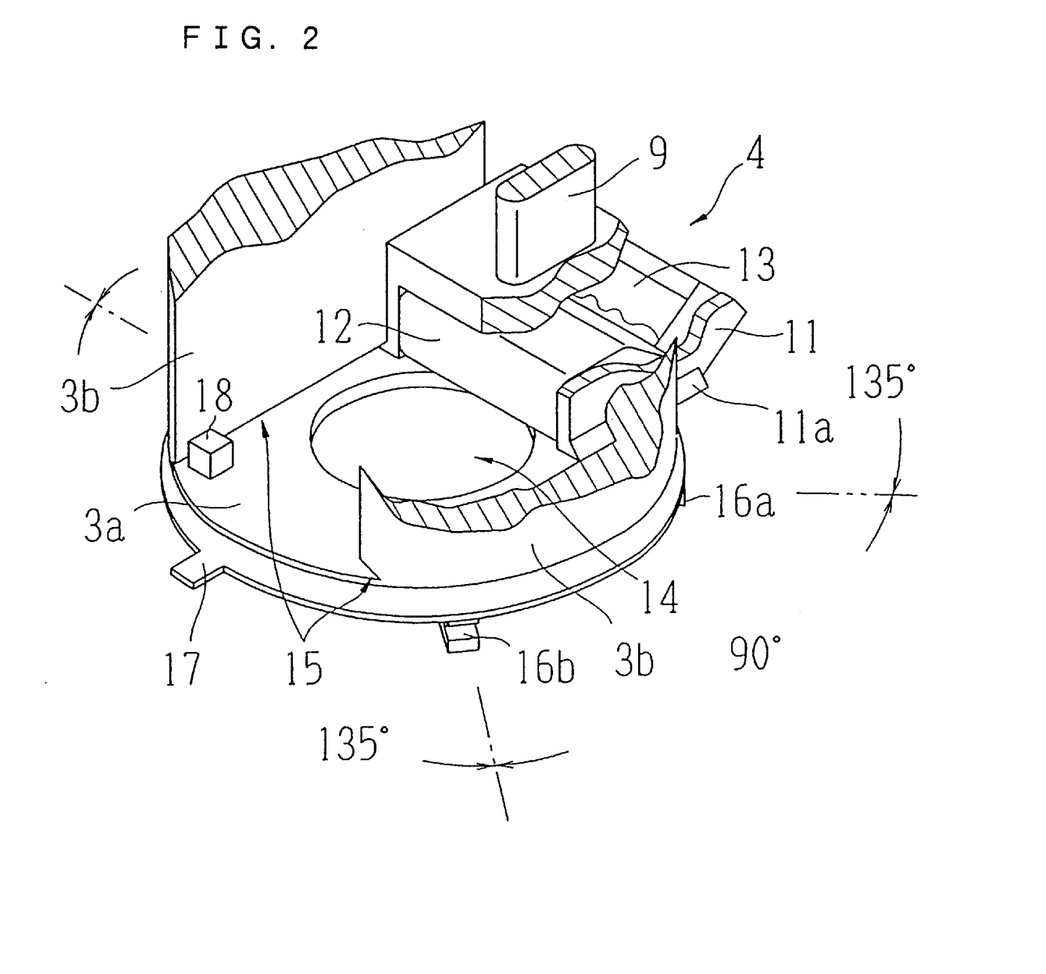
FIG. 2 is a perspective view of the main part around a cutting head part.

FIG. 2 is a perspective view partially in cross section of the main part of the cutting head part 4 and the bottom part of the base box part 3. The cutting head part 4 is constituted by a head part body 11, a cornea pressing part 12, and a blade 13. The head part body 11 is provided with a guiding projecting part 11a for moving the cutting head part 4 along a guide groove 15 described below. A mineral blade having mineral such as diamond, sapphire and the like as a cutting edge or a metal blade having stainless steel and the like as a cutting edge can be used as the blade 13.

An opening 14 through which the part of the cornea of a patient' eye to be incised during a surgical operation is protruded is made in the center of the bottom plate 3a of the base box part 3. A guide groove 15 in which the guiding projecting part 11a of the head part body 11 is fitted is made inside each of two side support columns 3b and hence the head part body 11 is guided by the guide grooves 15 and is straight moved. Reference numerals 16a, 16b, and 16c denote three projecting parts provided on the bottom plate 3a of the base box part 3 and are inserted into three notches 23a, 23b, and 23c made in a suction part 2 described below to rotatably connect the whole base part 1 to the suction part 2.

Reference numerals 17 and 18 denote stopper parts and the stopper part 17 limits the rotation of the base part 1 in cooperation with stopper receiving parts 25a and 25b described below. Since the rotation of the base part 1 is limited, when the peripheral part of the cornea is incised by rotating the blade 13, a part which is not cut by the blade 13 is formed to ensure a hinge part for preventing a flap from being completely separated from the cornea of the patient's eye. Therefore, the sizes and the positions of the stopper part 17 and stopper receiving parts 25a and 25b are set in such a way that they determine the size and the position of the hinge part to be formed in the cornea. A stopper part 18 for limiting the straight movement of the cutting base part 4 is provided inside each of two side support columns 3b so as to ensure the hinge part when the cornea is cut linearly by the straight movement of the cutting base part 4. The position of the stopper part 18 is set in such a way that it determines the size of the hinge part.

Figure 3:
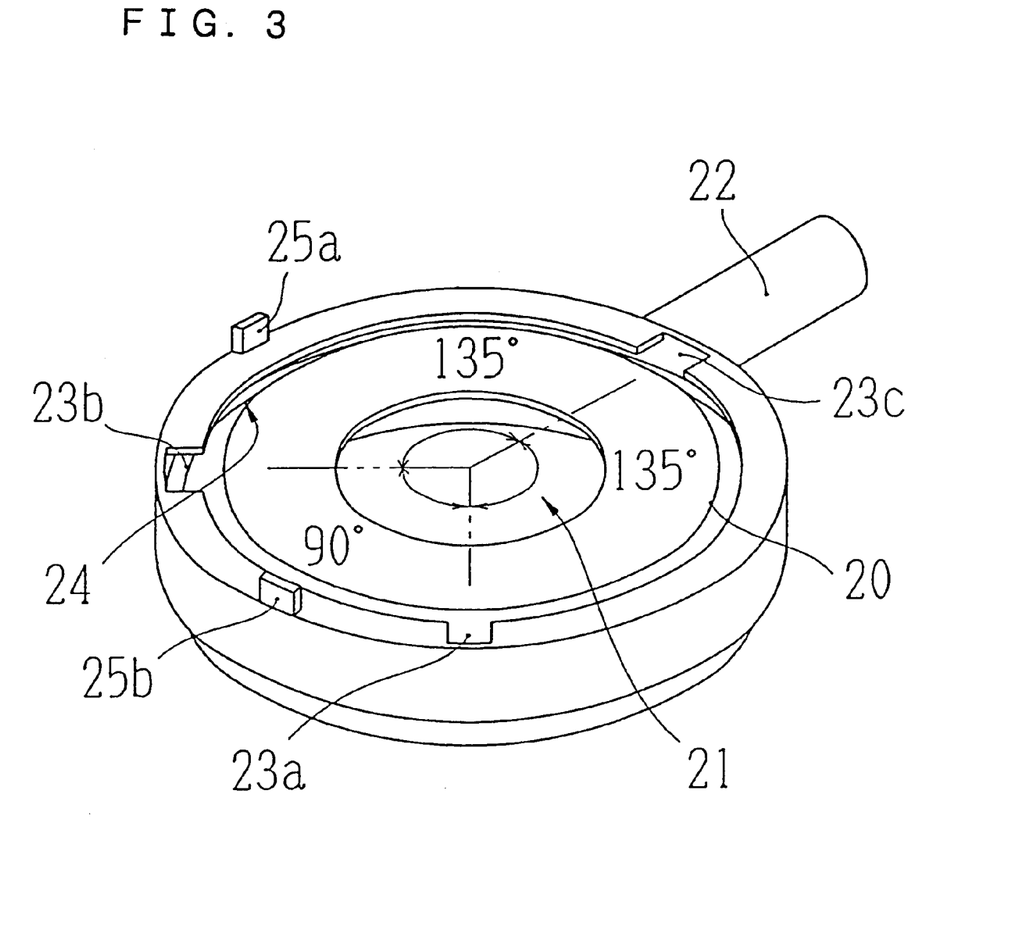
FIG. 3 is a perspective view of the main part of a suction part.

FIG. 3 is a perspective view of the main part of the suction part 2. A reference numeral 20 denotes a suction ring, 22 denotes a vacuum tube, 23a, 23b, and 23c denote notches and 24 denotes a rotation guide groove.

An opening 21 is made in the center of the suction ring 20 and the suction ring 20 is put into contact with the peripheral part (from the limbus of the cornea to a conjunctiva) of the cornea of the patient's eye and is made a base for the base part 1. The vacuum tube 22 is a tube for discharging air between the suction ring 20 and the peripheral part of the cornea of the patient's eye and is connected to a pump which is not described. The suction ring 20 is attracted by suction and fixed to the peripheral part of the patient's eye because the air between the suction ring 20 and the peripheral part of the patient's eye is discharged. In this respect, the vacuum tube 22 may be a solid body so that a surgical operator can hold it and, in this case, the surgical operator can also easily determine and stabilize the position of the suction ring 20 by holding the vacuum tube 22.

The notches 23a, 23b, and 23c and the rotation guide groove 24 are used for rotatably connect the base part 1 to the suction part 2. The blade 13 is rotated around the center of the opening 21 by inserting the projecting parts 16a, 16b, and 16c into the notches 23a, 23b, and 23c and by rotating the base box part 3 along the rotation guide groove 24. In the rotation of the blade 13, if the notches 23a, 23b, and 23c and the projecting parts 16a, 16b, and 16c corresponding thereto are arranged at equal intervals of 120 degrees, the base part 1 may be removed at the position other than the position where the base part 1 is inserted and hence the rotational movement may be stopped while the blade 13 is being rotated. Therefore, in the present embodiment, angles between the notches 23a, 23b, and 23c (projecting parts 16a, 16b and 16c) are made different angles, 90 degrees, 135 degrees, and 135 degrees, whereby the base part 1 can be removed only at a predetermined position.

Reference numerals 25a and 25b are stopper receiving parts and limit the movement of the stopper part 17 described above to limit the rotation angle of the base part 1, whereby the part to be the hinge part is not cut out by the blade 13 and is left.

In the cornea surgical operation apparatus having a constitution described above, the motion thereof will be described with reference to an illustration relating to the position of the blade shown in FIG. 4.

The surgical operator marks the cornea of the patient's eye by a tool like a marker not described so as to easily position the flap after the operation. Further, the operator sets the center of the opening 21 at the center of the pupil of the patient's eye while checking the slant state of the suction ring 20, the position of the center of the pupil and the like.

After the operator sets the suction ring 20, while holding the position and the slant posture of the suction ring 20, the operator operates a pump not described to discharge the air in the suction ring 20 (in the gap between the suction ring 20 and the peripheral part of the cornea) via the vacuum tube 22, thereby reducing the pressure. When the pump detects that the pressure in the suction ring 20 is reduced to a predetermined value, it keeps the pressure. Therefore, the suction ring 20 is fixed to the peripheral part of the patient's eye.

After the suction ring 20 is fixed, the base part 1 is set on the suction part 2. The projecting parts 16a, 16b, and 16c of the base box part 3 are inserted into the notches 23a, 23b and 23c corresponding thereto. The position of the blade 13 at this time (setting initial position) is shown by dotted lines $S_{SET}$ in FIG. 4(a).

Figure 4A:
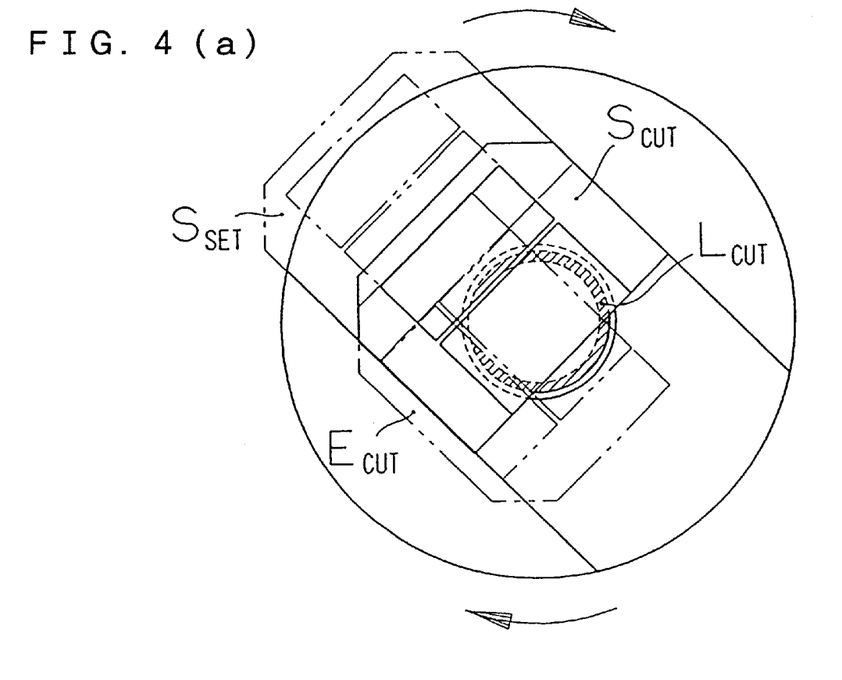
FIGS. 4(a) and 4(b) are illustrations relating to the position of a blade.

After the surgical operator sets the base part 1 on the suction part 2, the operator operates a foot switch not described to rotate the drive motor 5 and straight moves the cutting head part 4 to put the cutting edge of the blade 13 into contact with the cornea of the patient's eye and then further moves slightly the cutting head part 4 so as to slightly apply pressure to the cornea of the patient's eye (shown by solid lines $S_{CUT}$ in FIG. 4 (a)). It is essential that this position (the cutting initial position) is set to such an extent that a Bowman membrane can be incised by moving the blade 13 by the rotation operation described below. This position can be set by the visual checking of the surgical operator, however, it may be easily set by detecting the amount of movement of the cutting head part 4 and displaying the amount of movement. Further, it is also recommended that a distance from the setting initial position to the cutting initial position is previously memorized in a controlling part and the like of the drive motor and the cutting head part 4 is automatically moved.

After the surgical operator moves the blade 13 to the initial cutting position, the surgical operator rotates the base box part 3 to incise the cornea of the patient's eye as shown by shaded part $L_{CUT}$ in FIG. 4(a), whereby the Bowman membrane as well as the epithelium of the cornea are incised. The rotational incision by the blade 13 is started at the cutting initial position $S_{CUT}$ and is ended at the cutting position $E_{CUT}$ where it is limited by the stopper part 17 and the stopper receiving parts 25a and 25b.

Figure 5A:
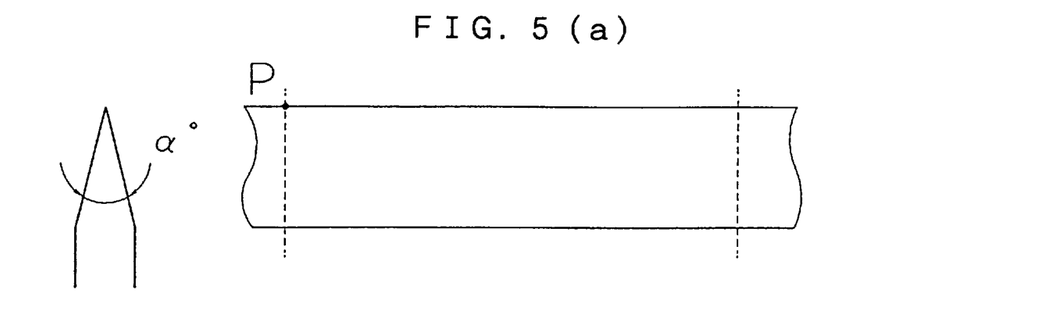
FIGS. 5(a), 5(b), and 5(c) are illustrations relating to the cutting angle of a blade.
Figure 5B:
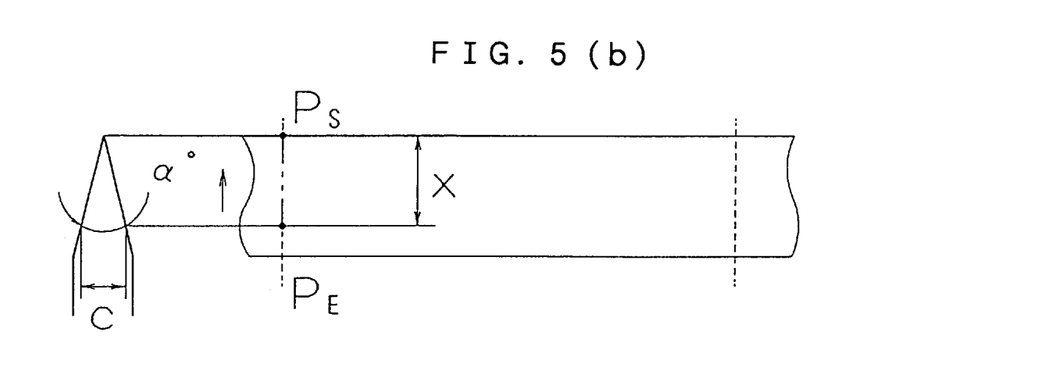
Figure 5C:
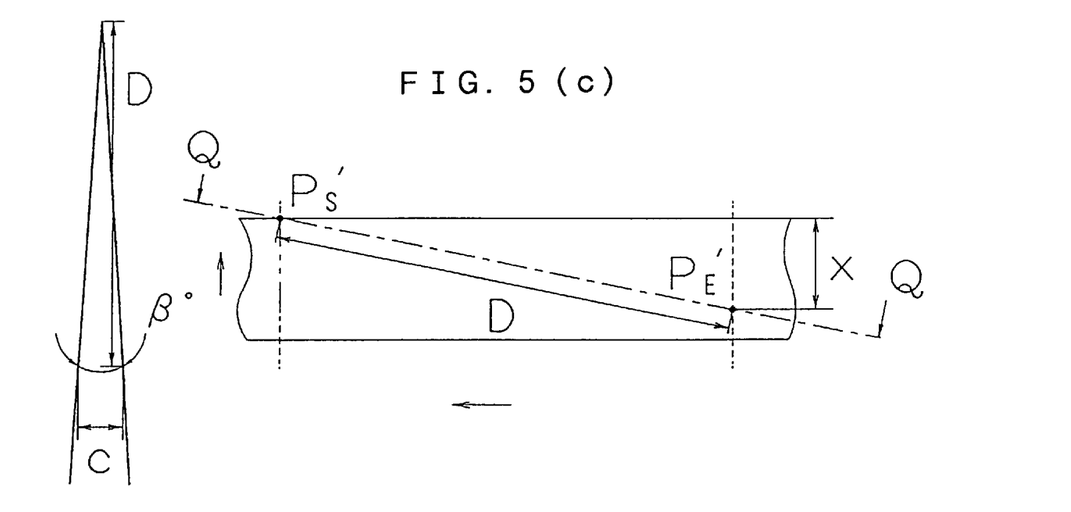

The reason why a considerable hard Bowman membrane can be incised by the rotation of the blade 13 will be described with reference to FIG. 5. FIG. 5 is an illustration relating to the cutting angle of the blade. FIG. 5(a) is a plan view and a cross sectional view of the blade, FIG. 5(b) is an illustration of the cutting angle when the blade is straight moved and FIG. 5(c) is an illustration of the cutting angle when the blade is straight moved while it is being slid in the transverse direction. In this respect, the mounting angle of the blade is the same in FIG. 5 (b) and FIG. 5(c).

Assuming that a cutting distance (feed of cutting edge) is "X", and that the thickness of the cutting edge of the blade when the blade cuts the distance X is "C". When the blade is straight moved as shown in FIG. 5(b), a given contact point P is moved relatively along the path $P_S$–$P_E$ on the blade and the distance of movement of the blade becomes X.

Therefore, the cutting angle thereof becomes α which is the same cutting angle shown in FIG. 5(a).

In contrast to this, when the blade is straight moved while it is being slid in the transverse direction as shown in FIG. 5(c), the point P is moved relatively along the path $P'_S$–$P'_E$ on the blade and the distance of movement of the blade becomes D. The actual cutting angle β in this case becomes sharper than the cutting angle α because it is shaped like the cross section of the cutting edge viewed from the direction of an arrow Q which intersects the path $P'_S$–$P'_E$ at right angle. That is, the same results can be obtained as is the case where the blade having a cutting blade shape of cutting angle β is straight moved.

Therefore, the incision by the rotation of the blade 13 around the center of the opening 14 results in the incision by sliding the blade 13 in the transverse direction with respect to the cornea (the initial contact point of the cutting edge moves in the same path of $P'_S$–$P'_E$). Therefore, the hard Bowman membrane can be considerably easily incised.

Figure 4B:
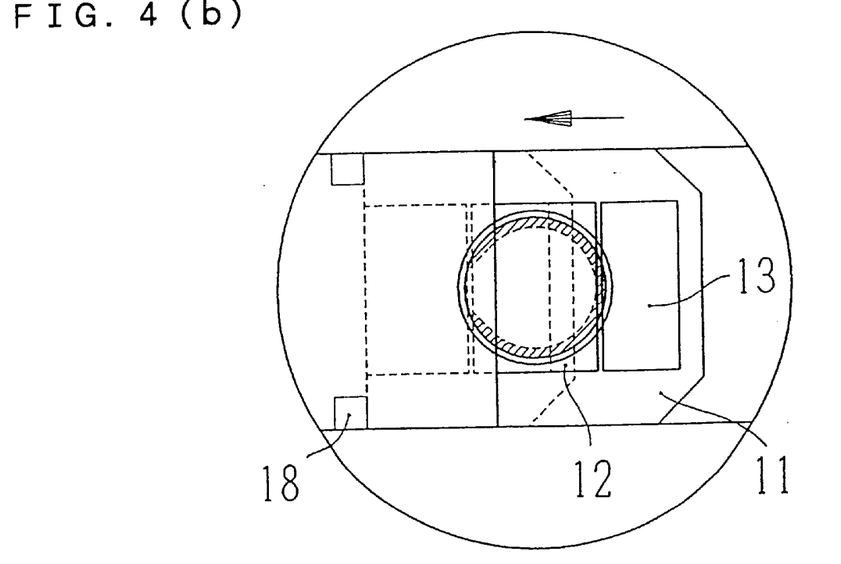

After the Bowman membrane can be incised by the rotation of the base box part 3, the base box part 3 is rotated in an opposite direction to arrange the blade 13 at the position shown in FIG. 4(b) (linear cut initial position). The linear cut initial position is located in the direction opposite to the hinge to be formed on the end part of the cornea and the surgical operator can easily position the blade 13 by previously marking the base box part 3 and the suction part 2.

After the surgical operator arranges the blade 13 at the linear cut initial position, the surgical operator presses the foot switch to drive the drive motor 5, thereby sliding the blade 13 along the guide groove 15 and incising the cornea. The cutting base part 4 is slid and put into contact with the stopper part 18 and is stopped there and hence the cornea of the patient's eye can not be incised into a layer with the hinge part left. In this respect, it is more preferable that a sensor for detecting the contact of the cutting base part 4 with the stopper 18 is provided and that it stops automatically the drive motor 5 when the cutting base part 4 is put into contact with the stopper part 18.

As described above, since the hard Bowman membrane of the cornea of the patient's eye is already incised by the rotational operation, the stroma of the cornea can be incised without vibrating the blade 13 and the incised cross section can be made uniform. Further, since the Bowman membrane and the stroma of the cornea can be incised by the same blade, each of incision which is performed by a different method is suitably performed. The changing of a mechanism or a blade is not required and effort is saved, which can reduce the load of the surgical operator and an operation time.

After the surgical operator finishes forming the flap by incising the cornea, the surgical operator removes the base part 1 and the suction part 2 and then ablates the stroma of the cornea by a laser and restores the flap, which is the end of the surgical operation.

Figure 6A:
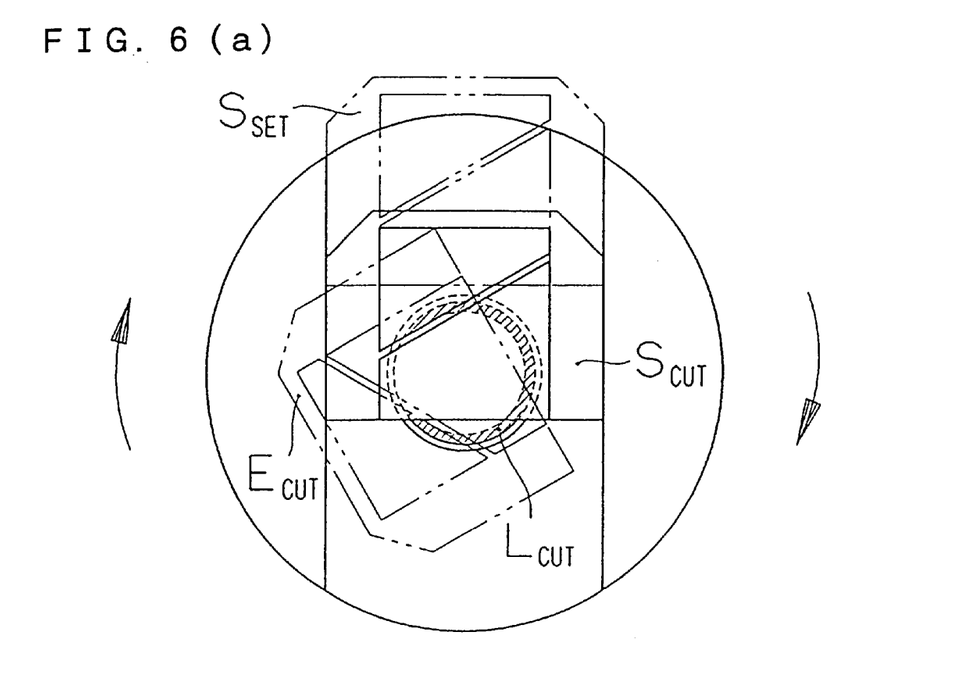
FIGS. 6(a) and 6(b) are illustrations relating to the shape of a blade and the position of the blade of the modified embodiment.
Figure 6B:
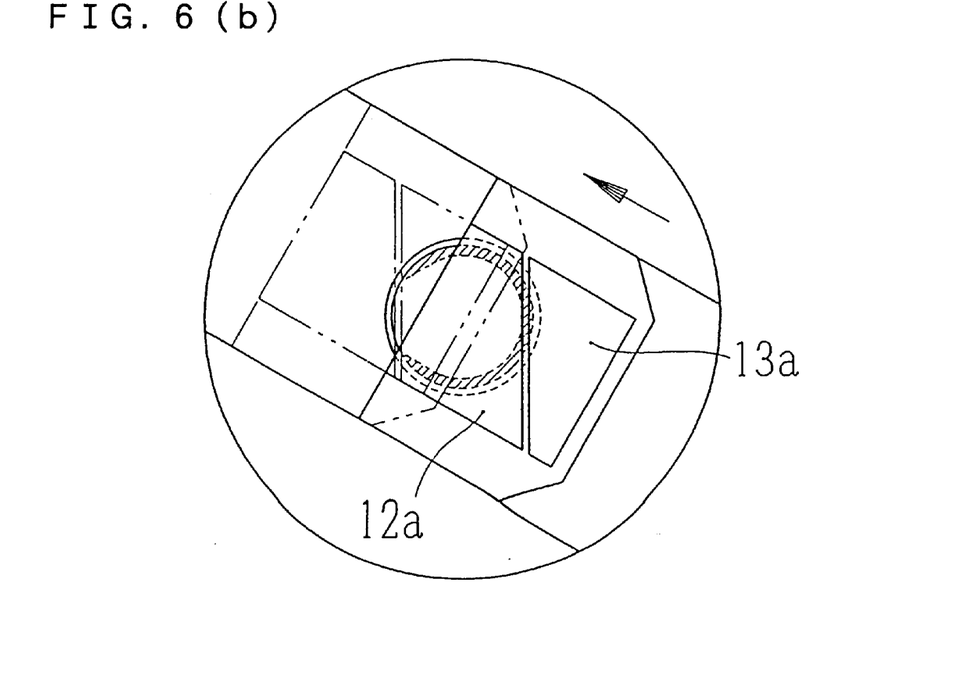

Although the cutting edge of the blade 13 is set vertical to the direction of travel of the linear cut in the present embodiment, the shape of the cutting edge of the blade 13a may be set slantwise with respect to the direction of travel of the straight movement. In this case, although the rotational incision is the same as in the embodiment, when the blade 13a is straight moved, since the cutting edge of the blade 13a incises the cornea of the patient's eye while it is being slid in the transverse direction with respect to the direction of travel, as described above, it can incise the cornea with a sharper cutting angle than the cutting angle of the actual cutting edge and hence it can more easily incise the cornea.

Further, although the blade is moved by the drive motor in the linear cut in the present embodiment, it can be moved manually and the rotational incision may be performed by moving the blade by the drive motor.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A cornea surgical operation apparatus for incising a cornea of a patient's eye into a layer, the apparatus comprising:

a suction ring part having a circular opening with a center, the suction ring part adapted to be fixed to a peripheral part of the cornea through a vacuum created by suction;

a base part including a cornea press means for pressing the cornea nearly flat within the opening, a blade for cutting the cornea, and a movement unit for moving the blade from a setting position to an initial cutting position and for moving the blade linearly so that it passes through the center of the suction ring part's circular opening; and a base rotating mechanism configured to rotate the base part so that the blade is adapted to incise at least an epithelium of the cornea and a Bowman membrane in a circumferential edge of the opening, the base rotating mechanism including stoppers for limiting the rotation of the base part, the base rotating mechanism holding the base part on the suction ring part so that the base part is rotatable with respect to the suction ring part.

2. The cornea surgical operation apparatus according to claim 1, wherein the base part includes a stopper for restricting linear movement of the blade.

3. The cornea surgical operation apparatus according to claim 1, wherein the base rotating mechanism holds the base part on the suction ring part so that the base part is rotatable and detachable with respect to the suction ring part.

4. The cornea surgical operation apparatus according to claim 1, wherein said blade has a cutting edge made of a mineral.

5. The cornea surgical operation apparatus according to claim 1, wherein the base rotating mechanism holds the base part on the suction ring part so that the base part is rotatable about the center of the circular opening.

6. The cornea surgical operation apparatus according to claim 1, wherein said blade has a cutting edge made of a metal.

7. A cornea surgical operation apparatus for incising a cornea of a patient's eye into a layer, the apparatus comprising:

fixing means having an opening put into contact with the surface of the cornea and for being fixed to a peripheral part of the cornea with said opening as a center;

press means for nearly flat pressing the cornea protruded from said opening;

a blade for cutting out the cornea pressed into a nearly flat shape by said press means;

movement means for moving said blade in such a way that it passes a center of said opening;

rotation means for rotating said blade movable at least to a Bowman membrane by said movement means with the center of said opening as the center of rotation; and a box provided with said press means, said blade and said movement means, wherein said rotation means is provided with rotation guide means for guiding rotation of said box with respect to said fixing means.

8. The cornea surgical operation apparatus according to claim 7, further comprising connection/disconnection means for connecting/disconnecting said box to/from said fixing means at a predetermined position of rotation.

9. A method of using a cornea surgical apparatus, comprising the steps of:

centering a circular opening of a suction ring part on a pupil of an eye;

creating a vacuum relative to atmosphere between the suction ring part and a peripheral part of the cornea thereby affixing the suction ring part to the cornea;

attaching a base part to the suction ring part;

placing a blade in the base part in a predetermined set position so that the blade is not in contact with the cornea;

moving the blade from the set position to an initial rotational cutting position thereby placing the blade in contact with the cornea so as to put a pressure on the cornea and allow an incision of a Bowman membrane to be made;

memorizing a distance between the set position and the initial cutting position;

activating a rotating mechanism to rotate the cutting blade from the initial rotational cutting position in a first rotational direction to an end cutting position thereby incising the Bowman membrane and an epithelium of the cornea;

rotating the cutting blade in a second rotational direction opposite the first rotational direction, thereby placing the cutting blade in a predetermined initial linear cut position;

moving the cutting blade linearly form its initial linear cut position to incise the cornea linearly thereby forming a flap on the cornea;

removing the base part from the suction ring part; and removing the suction ring part from the cornea.

* * * * *